US009164656B1

(12) United States Patent
Keller

(10) Patent No.: US 9,164,656 B1
(45) Date of Patent: Oct. 20, 2015

(54) GRAPHICAL DISPLAY FOR SCHEDULING AND MONITORING TASKS

(71) Applicant: Daniel S. Keller, San Francisco, CA (US)

(72) Inventor: Daniel S. Keller, San Francisco, CA (US)

( * ) Notice: Subject to any disclaimer, the term of this patent is extended or adjusted under 35 U.S.C. 154(b) by 75 days.

(21) Appl. No.: 13/737,444

(22) Filed: Jan. 9, 2013

(51) Int. Cl.
*G06F 3/0481* (2013.01)

(52) U.S. Cl.
CPC .................................. *G06F 3/04817* (2013.01)

(58) Field of Classification Search
CPC ........................... G06F 3/0481; G06F 30/4817
USPC ................................................. 715/772, 764
See application file for complete search history.

(56) References Cited

U.S. PATENT DOCUMENTS

| | | | |
|---|---|---|---|
| 5,519,606 A * | 5/1996 | Frid-Nielsen et al. | 705/7.19 |
| 5,559,875 A * | 9/1996 | Bieselin et al. | 379/202.01 |
| 5,570,109 A * | 10/1996 | Jenson | 715/823 |
| 5,634,100 A * | 5/1997 | Capps | 705/7.12 |
| 5,659,768 A | 8/1997 | Forbes et al. | |
| 5,761,646 A * | 6/1998 | Frid-Nielsen et al. | 715/769 |
| 5,895,451 A | 4/1999 | Yamade et al. | |
| 6,380,953 B1 | 4/2002 | Mizuno | |
| 6,442,527 B1 * | 8/2002 | Worthington | 705/7.19 |
| 6,661,438 B1 * | 12/2003 | Shiraishi et al. | 715/835 |
| 6,871,195 B2 * | 3/2005 | Ryan et al. | 706/46 |
| 6,892,346 B1 | 5/2005 | Lamb et al. | |
| 7,283,927 B2 | 10/2007 | Delargy | |
| 7,301,463 B1 * | 11/2007 | Paterno | 340/573.1 |
| 7,313,767 B2 | 12/2007 | Mak | |
| 7,346,705 B2 * | 3/2008 | Hullot et al. | 709/238 |
| 7,747,966 B2 | 6/2010 | Leukart et al. | |
| 7,757,181 B2 | 7/2010 | Pan et al. | |
| 7,814,055 B2 | 10/2010 | Hullot et al. | |
| 7,818,143 B2 | 10/2010 | Delargy | |
| 7,818,144 B2 | 10/2010 | Delargy | |
| 7,865,840 B2 | 1/2011 | Matsuzawa et al. | |
| 7,921,026 B2 | 4/2011 | O'Cull et al. | |
| 7,924,283 B1 | 4/2011 | Hao et al. | |
| 2003/0020599 A1 * | 1/2003 | Somers et al. | 340/309.15 |
| 2006/0053035 A1 * | 3/2006 | Eisenberg | 705/2 |
| 2006/0069604 A1 * | 3/2006 | Leukart et al. | 705/9 |
| 2006/0184943 A1 * | 8/2006 | DelMonego et al. | 718/100 |
| 2007/0129983 A1 * | 6/2007 | Scherpbier et al. | 705/8 |
| 2014/0157142 A1 * | 6/2014 | Heinrich et al. | 715/744 |

* cited by examiner

*Primary Examiner* — Phenuel Salomon
(74) *Attorney, Agent, or Firm* — David Pressman

(57) ABSTRACT

A portable, computing device (100) schedules and monitors tasks and their state of completion during a work period. The device includes a touch-responsive graphical display (102). At the start of and during a work period, an operator (400) enters tasks into the device. Task icons (118, etc.) move across the screen at positions representative of the time. A central "bridge" indicator (124) marks the current time. When a task is due, its icon approaches the bridge. If the icon coincides with the bridge, the task is late and a portion of its icon changes color, indicating that the task is late. The display can be scrolled to left and right to enable "looking ahead" and back. The display can also be pinched and spread to reveal in a smaller or larger time-scale the workday contents. The device communicates data and instructions with a remote server (405) wirelessly.

31 Claims, 7 Drawing Sheets

GRAPHICAL DISPLAY FOR SCHEDULING AND MONITORING TASKS

BACKGROUND

Prior Art

In the past, persons who had tasks or projects to do scheduled and monitored them on manually produced paper or wall charts, such as the well-known Gantt bar chart. In this chart, horizontal bars indicating start and finish dates of various parts of a project were arranged on a horizontal calendar. The bars extended horizontally in a vertical stack. The bars depicted the flow of work required to complete a project. They drew a vertical line representing the current date over all the bars so that viewers could note the relative current state of completion of each task. This type of chart and variations on it were widely used in the past. These charts were later computerized and many are still in use today. Some are available on hand-held computing devices. While useful in planning tasks, I have found that these prior-art charts are inflexible and not adaptable to some situations.

The following is a list of some possibly relevant references that show prior art scheduling apparatus and methods. Following this list I provide a discussion of these references.

| Pat. or Pub. Nr. | Kind Code | Issue or Pub. Date | Patentee or Applicant |
| --- | --- | --- | --- |
| 5,659,768 | B1 | 1997 Aug. 19 | Forbes et al. |
| 5,895,451 | B1 | 1999 Apr. 20 | Yamade et al. |
| 6,380,953 | B1 | 2002 Apr. 30 | Mizuno |
| 6,661,438 | B1 | 2003 Dec. 9 | Shiraishi et al. |
| 6,892,346 | B1 | 2005 May 10 | Lamb et al. |
| 7,283,927 | B2 | 2007 Oct. 16 | Delargy |
| 7,313,767 | B2 | 2007 Dec. 25 | Mak |
| 7,747,966 | B2 | 2010 Jun. 29 | Leukart et al. |
| 7,757,181 | B2 | 2010 Jul. 13 | Pan et al. |
| 7,814,055 | B2 | 2010 Oct. 12 | Hullot et al. |
| 7,818,143 | B2 | 2010 Oct. 19 | Delargy |
| 7,818,144 | B2 | 2010 Oct. 19 | Delargy |
| 7,865,840 | B2 | 2011 Jan. 4 | Matsuzawa et al. |
| 7,921,026 | B2 | 2011 Apr. 5 | O'Cull et al. |
| 7,924,283 | B1 | 2011 Apr. 12 | Hao et al. |

Forbes shows a computerized graphical staff scheduler that represents each worker's time on duty. The purpose of this scheduler is to plan and track each worker's time during a shift. At the bottom of the display is an indication showing how many staffers are working and how many are on break on an hour-by-hour basis. This display is not dynamically updated over time and it does not use icons to represent tasks or individuals.

Yamade shows an electronic display of an appointment book. Morning, afternoon, and evening appointments are colored green, yellow, and blue, respectively. The format of the display is that of conventional paper appointment books, with the times of day followed by textual descriptions of scheduled events and activities. An algorithm looks up events in data storage, orders them, and decides which color to apply based on the event's time of day. The colors are not updated to show event status, e.g. whether an event has been completed. In addition, icons are not used to represent events or objects.

Mizuno shows a graphical user interface for displaying manufacturing steps on a scrollable time axis. The user can scroll the display forward or backward in time in order to see more information. The time scale of the display is expanded or compressed in predetermined increments by selecting one of several buttons on the display. The ability to use one's fingers to "pinch" or "spread" the display, as is found in present-day computing devices, is not shown.

Shiraishi shows a display and portable information processing apparatus. Tasks are shown in a spatial layout on a display screen. Icons depicting buildings, flowers, etc., serve as metaphors to represent different types of events. Its display updates dynamically over time and serves as a planner, showing meetings and events over time. Icons are sized according to the duration of what they represent, e.g. meetings. Thus this is a general purpose personal organizer.

Lamb shows a method for generating an image of a calendar page in an optimized, minimum amount of screen area on a hand-held display. Events are shown as lines of text in a vertical arrangement where each line represents an hour of the day, e.g. "12:00 meeting with Tara Jones" or the start or end time of a particular event. This system does not provide detailed task lists to support accurate execution of a job role; rather it provides an ordinary appointment calendar function on the screen of a handheld device.

Delargy, in patents U.S. Pat. No. 7,283,927 and its divisions U.S. Pat. No. 7,818,143 and U.S. Pat. No. 7,818,144, shows a hand-held activity recording module comprising a grid with colored squares representing blocks of time. As in the above-described Gantt chart, the duration of a task is represented by the size of a colored block. Delargy's algorithm takes all of a worker's tasks and squeezes them into the time available, using its logic to decide how to order the tasks and how to resolve overlaps. Activities are grouped into columns and colors according to the type of activity that they are, rather than using a unique icon for each specific activity for a user to recognize. The primary purpose of this system is to record a worker's activities; it is not dynamic and does not update itself as time passes. Instead, it relies on the user to scroll up and down in the display to see what is due and when. It offers time management functionality but not to the level of the individual task.

Mak shows a system and method for presenting time related data on a small screen device. Mak uses text, not icons, to represent the events and appointments in a calendar or agenda, next to colored segments within a bar that represents time. The segment lengths are proportional to the items' durations. Thus this system resembles a paper appointment book with an accompanying time bar that represents visually which hours are occupied, which are free, and how long things last. The display is static and it does not update as time passes.

Leukart shows a user interface for providing task management and calendar information in a multitasking environment, i.e the task management display runs concurrently with the display of other processes such as word processors and the like. This system shares data with other processes in the computer such as a calendar and enables planning over days and weeks. It does update dynamically with a time scale that slides across the screen as time passes and the appearance of items, which are not represented by icons, does not change as deadlines arrive.

Pan shows a display with a hybrid view that includes both a schedule view of listed calendar items together with an overview strip that displays a compressed version of the schedule view. Its objective is to make obvious to the user both free (uncommitted) time and schedule conflicts in order to make time management easy. It does not leave the user to decide how to handle a plurality of tasks that fall at the same time, rather it is intended to help avoid such overlap.

Hullot shows a method of managing a calendar. The display has the appearance of a traditional appointment book, with a page for a day and a line on the page for each hour of the day. An event is shown as a colored region on that line. An event lasting more than one hour spans more than one line. No icons are used to represent predetermined tasks and the display does not update dynamically as time passes. A to-do list is included, but tasks are represented simply by some text with a checkbox. Thus this application is not for in-depth workflow and time management and task tracking.

Matsuzawa shows a cell phone-based, multimedia graphical display of a calendar containing events and time-related multimedia data that serves as a personal appointment book and diary. It uses icons arranged along a time axis to represent the various items in the user's calendar. When a user selects an icon, it generates and positions a pop-up window that shows details about the selected event. Icons and text are sized in order to maximize the information shown on the display. The display is organized as a personal diary, not a detailed job checklist.

O'Cull shows a timeline that is associated with a project schedule. It looks like a well-known, industry standard Gantt chart. A display shows the steps to be performed in conducting a project and how long each step takes in order to plan and manage a project. It does not use icons and does not update itself dynamically as time passes.

Hao shows a method for displaying a time-series data set. Data are represented as colored rectangles, not icons. Individual data elements are simple numerical values shown in sequences that represent change over time. Colors represent quantities, not task status, and the display does not update dynamically. The purpose of this system is to display large amounts of data such as stock market prices, resource consumption, or weather data that are collected over long periods of time and to present them so that trends and patterns are made visible.

Many jobs consist of numerous discrete tasks that must each be accomplished at a specific time or following specific intervals within the workday or work shift. Thus the above-described references are each useful for their intended purposes. However each has one or more disadvantages as noted. In general, the above-described systems are based primarily on traditional conceptual models including Gantt charts, appointment calendars, and to-do lists.

Often, tasks must be done at specific times or at specific intervals. In the case of nursing care, such tasks include at least the following:

Administering medications every four hours,

Hanging or replacing intravenous fluid bags when they run out after times determined by flow rates, Flushing catheters once per shift to reduce the chance of infection, and Setting up meal trays at specified mealtimes.

The nurse must remember to do each and every task at the proper time. Thus, time management in such jobs is challenging and essential. The mentally burdensome aspects of such work include at least the following requirements:

The nurse must keep track of all the tasks to make sure they are all completed,

When there are frequent interruptions, the nurse must remember to return to partially completed tasks, The nurse must budget time carefully, foreseeing task clusters and getting a head start on them, The nurse must prioritize effectively when several tasks are due at the same time and knowing which to tackle first. This requires knowing what all the tasks are in order to choose among them.

The nurse must choose appropriate times to take breaks from work, which means being able to foresee times when the demands are relatively light, and The nurse must delegate some of the tasks when a time crunch becomes especially severe. This is possible only when the set of tasks that need to be done at that moment are identified well enough that suitable subsets can be named and handed off to co-workers. This is more difficult than it sounds; the worker can't hand off part of a day's work to someone else without knowing what the parts of the work are.

To alleviate this mental burden, a variety of to-do list formats have been devised. The simplest is a handwritten list of tasks. A more complex type of to-do list organizes tasks into columns on paper or wallboard, with one column for each hour of the day. Using the column method is an improvement but still labor-intensive and requires attention when various situations arise. For example, if a patient is discharged, the nurse must remember to erase all the tasks for that patient that remain undone in their list.

SUMMARY

I provide a new scheduling system and method that overcomes at least some of the limitations of the prior art. In one aspect, my system comprises a hand-held, portable computing device with a display that shows what work to be done and work that is completed during a work period or shift. A plurality of task lists are arranged vertically on the display. Each task list is represented by a horizontal timeline that continually updates by moving leftward as time passes, as in the flow of a river. A central vertical line forms a "bridge" over all tasks and indicates the present time of day. Tasks to be done eventually are shown in a first color, tasks that are due soon are shown in a second color, and tasks that are completed are shown in a third color. Tasks that are overdue are shown in a fourth color. Typically, these colors are white, yellow, green and red, respectively.

In another aspect, the portable computing device has a touch-sensitive screen that permits manual selection of icons and other features on the screen and also enables scrolling of the display both horizontally and vertically. In addition, the display can be "pinched", i.e. two fingers are placed on the screen and moved together to compress the horizontal time scale shown so that a longer time interval is displayed, or the fingers spread apart to expand the time scale shown on the screen. The screen normally displays one hour of activity; however by using a pinching or spreading touch action, any time frame from minutes to the entire work shift is shown. The display can also be scrolled horizontally to show the past or future events.

The central vertical "present time" line moves with the task lists as the display is scrolled to show the present time on the timelines. When touched, an icon on the display causes the display to resume its default appearance, i.e. one hour of activity is shown and the vertical "present time" line is centered on the display. In another aspect, all activity of the hand-held device is synchronized with a central server that provides communication with one or more hand-held devices and other computers.

The central server serves as an archiving database for all activities as they are scheduled and performed. An individual daily schedule is entered at a computer terminal or on a hand-held device and then communicated to a predetermined hand-held device. The hand-held device reports all activity back to the server as each task is addressed. A plurality of handheld devices, each with its own schedule share data with a server.

For the nursing field, a metaphor and method is provided that overcomes these shortcomings and provides an effective model for helping nurses as well as others manage the mental burden of their complex, time-sensitive, task-structured jobs.

DRAWING FIGURES

Figure 1:
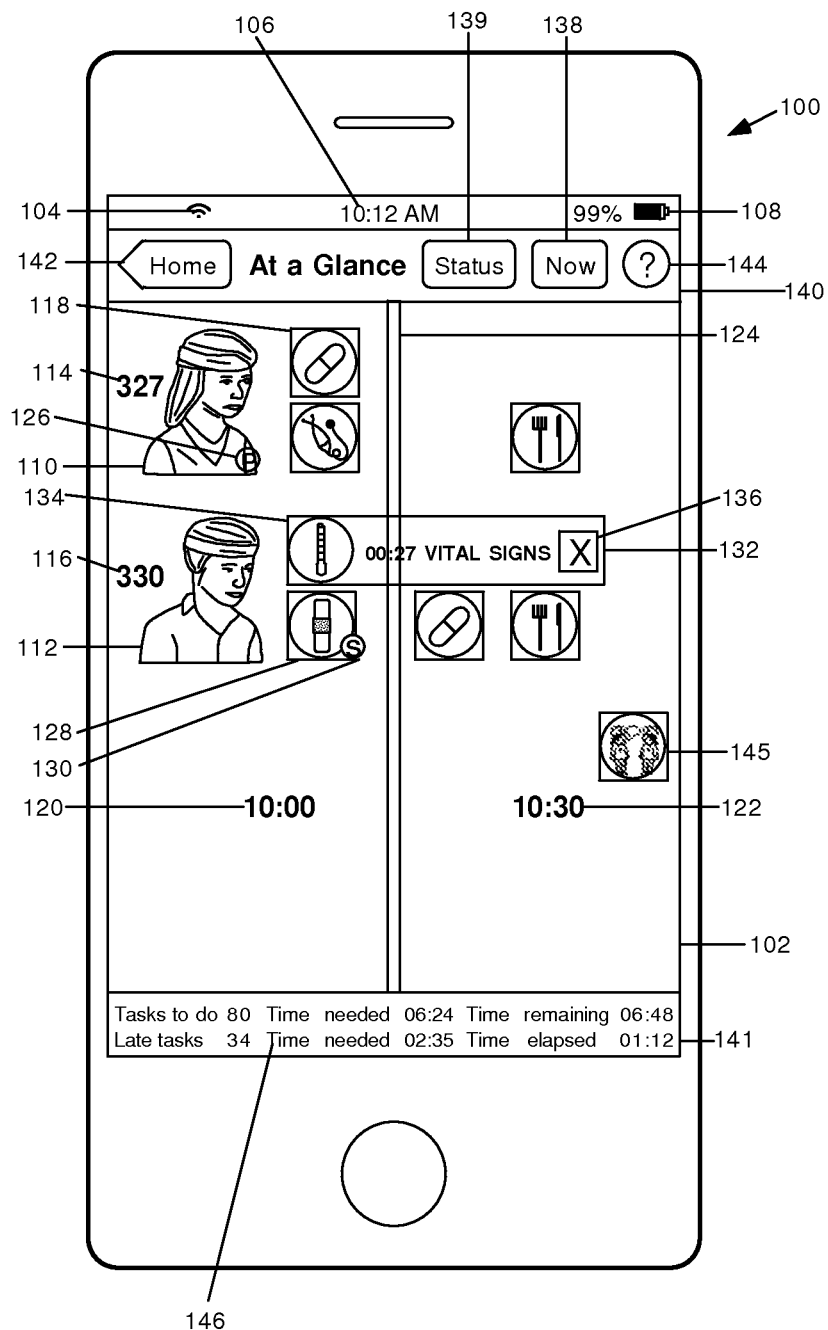
FIGS. 1 through 3 show the front touch screen of a hand-held scheduling device according to one aspect of one embodiment.

| DRAWING REFERENCE NUMERALS | | | |
|---|---|---|---|
| 100 | Device | 102 | Display |
| 104 | Icon | 106 | Time of day display |
| 108-112 | Icon | 114-116 | Indicia |
| 118 | Icon | 120-122 | Signpost |
| 124 | Bridge | 126 | Badge |
| 128 | Icon | 130 | Badge |
| 132 | Box | 134 | Icon |
| 136 | Touch square | 138-139 | Button |
| 140 | Box | 141 | Box |
| 142-144 | Buttons | 146 | Text and numbers |
| 200 | Finger | 300 | Thumb |
| 400 | Nurse | 405 | Server |
| 410 | Nurse | 415 | Computer |
| 500 | Data | 505 | Cache |
| 510 | Data pages | 515 | Data repository |
| 700 | Key | 705-710 | Buttons |
| 800 | Selector | 900-980 | Blocks |

Abbreviations
GUI Graphical User Interface ROT River of Time
Wi-Fi Trademark for radio protocol through which computing devices can communicate

FIRST EMBODIMENT

Figure 2:
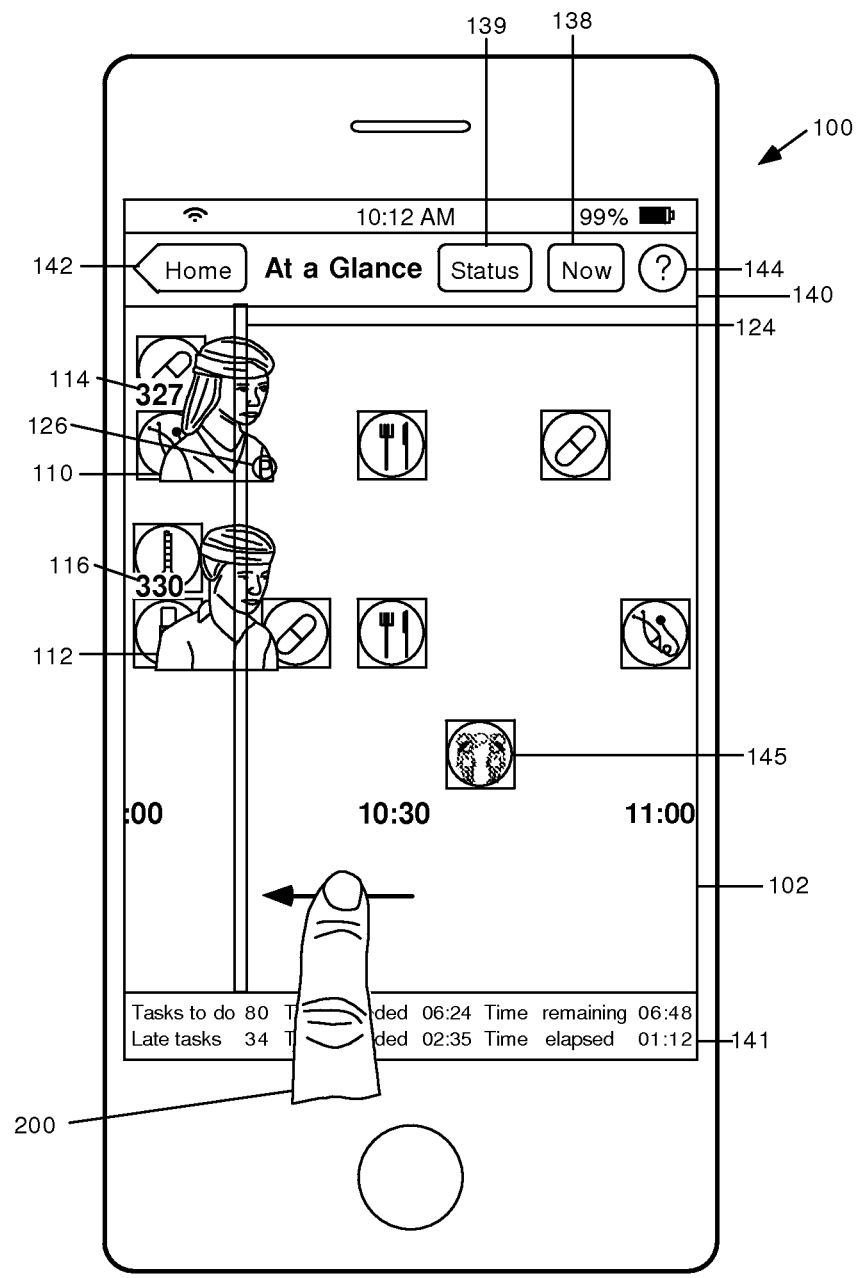
Figure 3:
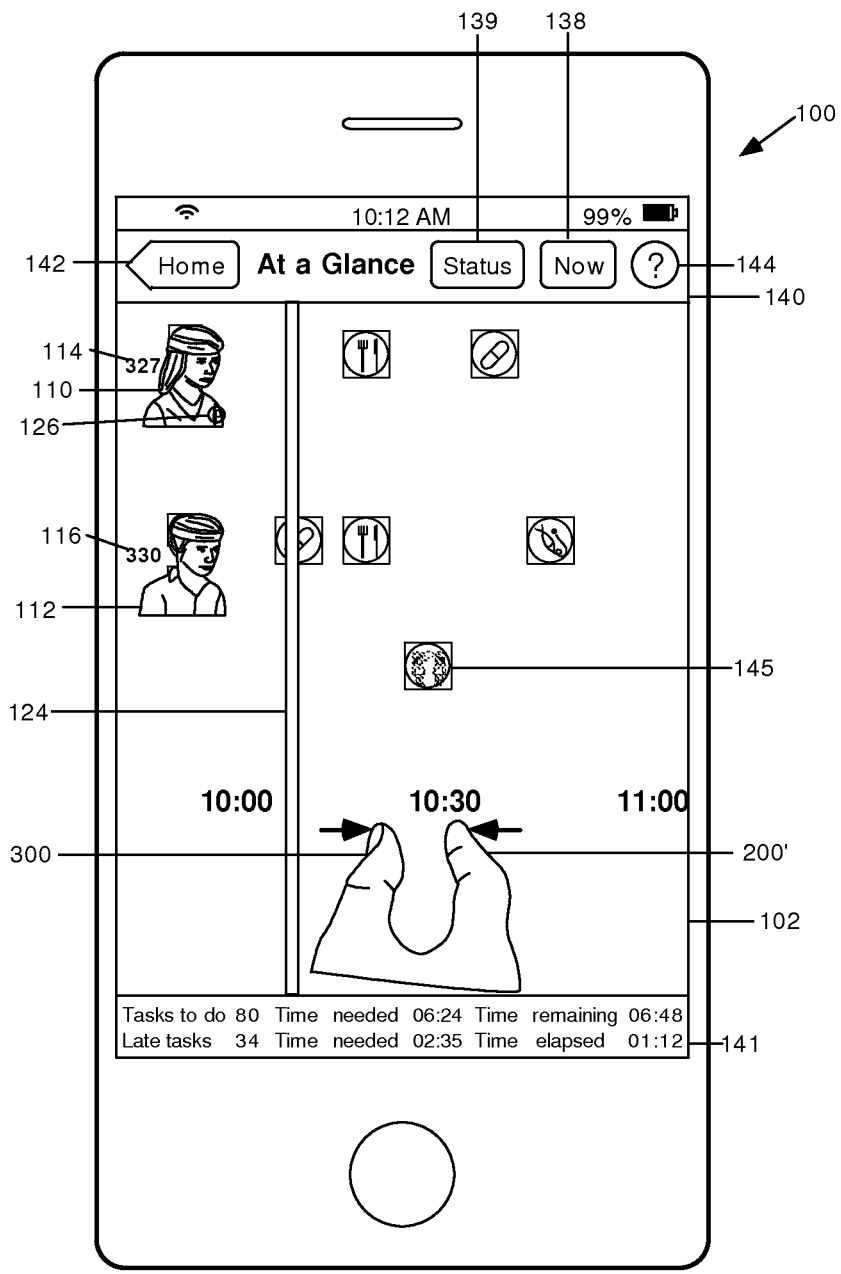

Description—FIGS. 1 through 3

In a first aspect of the present embodiment, a hand-held scheduling device is provided in a size that can be carried by a user. The device includes a touch screen display that is capable of recognizing one-finger and two-finger commands, i.e., a touch and a pinch or spread. In addition, the device includes a timer for keeping the time of day, and also has the capability for wirelessly interacting with a central server computer for sending and receiving commands and data. A wired connection between the device and the server is also possible and would work in an equivalent manner, but is not discussed in detail here. Devices that fulfill these requirements are the iPhone, iPod Touch, and iPad handheld computing devices sold by Apple Computer Company of Cupertino, Calif., USA. Other devices with similar capabilities can be used.

One metaphor for the present system is called the "River of Time" (ROT) and it is the basis for graphical user interfaces (GUIs) on handheld and other devices such as smart phones, personal digital assistants, and personal computers. In a compact area, the ROT conveys a great deal of information at a glance. The ROT metaphor is intuitive and obvious to use and most users find it helpful without training or explanation.

In one aspect, electronic displays that apply the ROT metaphor do so by means of ten features. I presently consider the first four more significant than the others, which add value and contribute to the system's effectiveness although the metaphor can function without them.

Features

A variety of features available in present-day touch screen displays make it possible to pack a large amount of information into a single GUI display. Principal among these features are icons and other indicia, some of which are touch-responsive.

Icons.

FIG. 1 shows a GUI on the front face of a hand-held computing and wireless communicating device 100 of the type mentioned above. A display 102 on device 100 contains various icons, i.e., graphical representations of things and events and text that is related to the functions of scheduling and monitoring tasks.

A well-known radio-frequency (rf) reception icon 104 is visible at the top of display 102; it indicates that the device is receiving an rf signal from a central computer or server. Such a signal is commonly termed a Wi-Fi signal. (WiFi is a trademark owned by the Wi-Fi Alliance of Austin, Tex., USA, for a wireless, i.e., radio, means and protocol through which computing devices can communicate.) Icon 104 shows three lines, the indication of a strong signal between device 100 and a remote server computer (discussed below). Fewer lines indicate a weaker signal and the absence of icon 104 indicates that there is no wireless communication between device 100 and an external server computer. The present time of day is shown at 106 and a battery indicator icon 108 indicates the state of charge of an internal battery that powers device 100.

A number of additional icons are shown in the central portion of display 102. A female icon 110 represents a female patient and a male icon 112 represents a male patient. Numeric indicia 114 and 116 indicate the respective room numbers, as in a hospital, where the patients are located. An icon 118 with an image of a capsule indicates a task in which medicine is to be given to the patient represented by icon 110. Wi-Fi and battery indicator icons, 104 and 108 respectively, patient identifying icons 110 and 112, and indicia 114 and 116 are normally fixed in position on display 102. Task icons such as the one indicated at 118 normally move from right to left, as described below. The remaining icons are discussed in detail below.

Time.

The second feature is the GUI's representation of time. In the ROT, time is represented by the display's horizontal axis. A number of signposts 120, 122 are calibrated in hours and minutes, although other calibrations can be used. The horizontal placement of an icon on this axis represents the deadline by which the task it represents must be completed. As time passes, the task icons "float" on this "river" of time. The river normally flows steadily from right to left. With it, the task icons move gradually from right to left. Because the handheld screen is small, the motion is too gradual to be visible.

"Now" Bridge.

The third feature is a "now" bridge indicator 124 that extends down the center of the display. Bridge 124 is a transparent yellow line, although other types of lines can be used. The location of bridge 124 normally remains fixed at the center of display 102 while the task icons 118, etc., float by from right to left beneath it. Tasks whose icons are to the right of bridge 124 are those whose deadlines have not yet arrived in time. Those to the left are tasks whose deadlines have passed. When a moving icon approaches bridge 124, the task that the icon represents is now due. The nurse performs the task and marks it done or completed, as described below. In the illustration, it is now 10:12 AM. Bridge 124 is thus nearly midway between the 10:00 AM signpost and the 10:30 AM signpost.

Task Status.

The fourth feature makes visible the status of tasks within this time context. The background color of a task is white, yellow, green, or red, depending on whether the task is yet to be done, is due within the next fifteen minutes, has been done, or is late in being done, respectively. The nurse indicates that a task is done by touching the icon for that task. The sequence of steps to mark a task done in one embodiment is: (1) touch the task's icon to pop up the task's detail box, (2) touch the detail box to switch to the Task Detail screen, (3) touch the Task Status checkbox in the Task Detail screen to mark the task done and turn its background green, and (4) touch the Back button in the Task Detail screen to return to the River of Time (Shift at a Glance) screen.

For example, when the task shown on icon 118 was yet to be done, it was on the right-hand side of bridge 124 and the corner background region between the circle and square of icon 118 was white. If the nurse indicates that the task has been completed by touching icon 118, the corner background region turns green. If the nurse fails to complete the task before icon 118 reaches bridge 124, the corner background region of icon 118 turns red. In the latter case, the nurse can complete the task and then touch icon 118 and its background color will change to green, indicating that the task has been done. Thus at a glance the nurse can see how much red is on the screen. Seeing many red icons tells the nurse they are falling behind; they should work faster or ask for help.

Organization.

The fifth feature is organizational; it categorizes the tasks by some shared characteristic. In the nursing example, this characteristic is the patient for whom the task is to be done. Each patient is represented by an icon as indicated at 110. Patient icons are arranged on the vertical axis and the icons for the tasks for each patient are horizontally aligned with their respective patient icon. For example, the top row contains all the icons representing the tasks to be done for Ms. X in room 327, the next row down is Mr. Y in room 330, and so on. If there are more patients than can fit on display 102 at one time, the contents of display 102 can be scrolled down to reveal additional patients, in well-known fashion for those familiar with touch screen operation. This screen arrangement helps the nurse to get an overall, at-a-glance sense of how much work is needed by whom and when.

Reminders.

The sixth feature of the present GUI serves to jog the user's memory. "Badges" are added to the patient icon or the task icon or both to serve as a reminder that special requirements apply.

On the Patient Icon.

For example, a patient may require "precautions". These are notations in the patient's chart, and perhaps on his hospital room door, that special care is required. For example, a patient may be deemed to be at risk for falls so the nurse must remember to support them when they move around. An additional indicium or "badge" 126 on icon 110 is a "P", indicating that precautions must be taken with this patient.

Another example of a precaution is termed "droplet precautions". This means that a patient could potentially spread infectious agents by coughing, sneezing, or talking, or during procedures such as suctioning or bronchoscopy. The badge on the icon reminds the nurse to wear a surgical mask to prevent exposure.

On the Task Icon.

Another application of this sixth feature with badges on icons is to use them on task icons. An icon 128 showing a bandage includes a badge 130 bearing an "S". Badge 130 alerts the nurse that supplies, e.g., a bandage, are required for this task. The nurse can see all the presently-due tasks that require supplies and so can save time by being reminded to gather all the supplies at once, rather than going back and forth to a stockroom for each task. Clustering of tasks and optimizing hall travel is difficult for many nurses but with this badge feature on their display it becomes easy and improves productivity. Similarly, a "D" badge means the task must be documented, and so forth.

Detail Box.

The seventh feature is a "detail box" 132 that is displayed when a task icon is tapped. In this an icon 134 contains a representation of a thermometer. When icon 134 is tapped, its rectangular outline expands to show more information, in this case the alphanumerics "00:27 Vital Signs". The box contains a description of the task, and the number of minutes remaining until its deadline is reached. Once the box is displayed, the user can tap on it to get a screen (not shown in this diagram) offering various operations on the task, especially "Mark as completed (done)". This colors the icon's background green as described in the fourth feature above. The nurse can also touch square 136, "X", to close the box, leaving only icon 134

Forward and Backward Time View.

FIG. 2 shows one aspect of the eighth feature, the ability to look forward and backward in time on display 102. This is done by dragging the task icons, 118, 128, 134, etc., bridge 124, and signposts 120 and 122 in the central part of display 102 to the left and to the right, respectively. The nurse drags the central portion of the contents of the display by sliding a finger 200 across its surface from right to left to reveal icons that are further in the future and beyond the right edge of the screen. This is, in effect, looking ahead in time to see what tasks will be coming due. Similarly, the nurse slides a finger across its surface from left to right to reveal icons that are further back in time, beyond the left edge of the screen. This is, in effect, looking back in time to see what tasks have been completed and whether any have been overlooked and are now overdue, i.e. whose backgrounds have turned red.

Patient icons 110 and 112, patient badges 126, and room numbers 114 and 116 remain fixed in their original positions, serving as labels for each patient's row of information and tasks, as the rest of the components within the central portion of display 102 are moved.

A "NOW" button 138 near the bottom of display 102 (near the top of display 102 in another embodiment) is used to reset display 102 to its original condition. To return to present time, the nurse taps "NOW" button 138 on display 102. This causes bridge 124 to return back to the center of display 102 and all movable icons on display 102 to return to their proper horizontal axis time location with respect to bridge 124.

Pinch and Spread.

FIG. 3 shows application of a ninth feature: the effect of "pinch" and "spread" gestures applied to display 102. This feature can be programmed on "multi-touch" displays, i.e., those that can detect two fingers simultaneously. To pinch means to place two fingers on the screen and slide them together. To spread is the opposite; the fingers are slid apart. FIG. 3 shows a thumb 300 and forefinger 200' moving together in contact with display 102, as indicated by arrows. The effect on the display of the pinch gesture is that the icons are shrunken and the time scale is compressed, rendering visible task clusters over time. Work bottlenecks can thus be foreseen. This also reveals open stretches when work breaks can be considered. The inverse gesture, finger spreading, enlarges the icons and reduces the span of time displayed. In effect, spreading increases the resolution of the image, revealing details such as badges (feature six) that were not visible when the display was pinched. Another way to describe it is that pinching is zooming out and spreading is zooming in. Slide, as well as pinch and spread, can be used separately or together. As above, display 102 is reset to its original scale when the nurse touches "NOW" button 138.

Buttons and Summaries.

FIG. 1 shows a tenth feature of the present GUI. A box 140 near the top of display 102 contains four icons: a "Now" button 138, a "Status" button 139, a "Home" button 142, and a "?" button 144 that causes a "Help" menu to be displayed in display 102.

A box 141 near the bottom of display contains several lines of informational text and numbers 146. These numbers help a nurse have a sense of progress in the current shift and whether they are getting ahead or falling behind. In this example, it is 10:12 a.m. and the nurse is working an eight-hour shift (the length of a typical shift, though sometimes this is ten or twelve hours) that started at 9:00 a.m. The six numerical summaries of the number and statuses of tasks are as follows, starting at the upper left:

(1) How many tasks with clear backgrounds are not late and remain to be done.
(2) How many hours and minutes it will take to do all the remaining undone tasks. The background color of box 141 turns red if it is larger than the number of minutes remaining in the shift.
(3) How many hours and minutes remain in the shift. In box 141, six hours and forty-eight minutes (6:48) remain. This was calculated as eight hours minus one hour and twelve minutes (8:00-1:12=6:48).
(4) How many tasks are late. This is the count of tasks with red backgrounds.
(5) How many hours and minutes are needed to complete the late tasks (the sum of their durations).
(6) How many hours and minutes have elapsed since the shift started. In box 141, this is one hour and twelve minutes (01:12) of an eight-hour work shift.

When pressed a first time, status button 139 causes box 141 to appear, showing the overall status of tasks remaining to be done and completed, along with the time available in which to complete the tasks. Status button 139 is normally blue, green, or another color that indicates tasks are being completed on schedule. When the time needed exceeds the time remaining, status button 139 turns red, alerting the nurse to this fact so action can be taken.

Home button 142 is not part of the ROT metaphor. Instead, it causes display 102 to display other functions of the software, described below, in which the ROT is embedded.

The "?" (Help) button 144, also not part of the ROT metaphor, accesses built-in or on-line help information that is shown in display 102.

Figure 4:
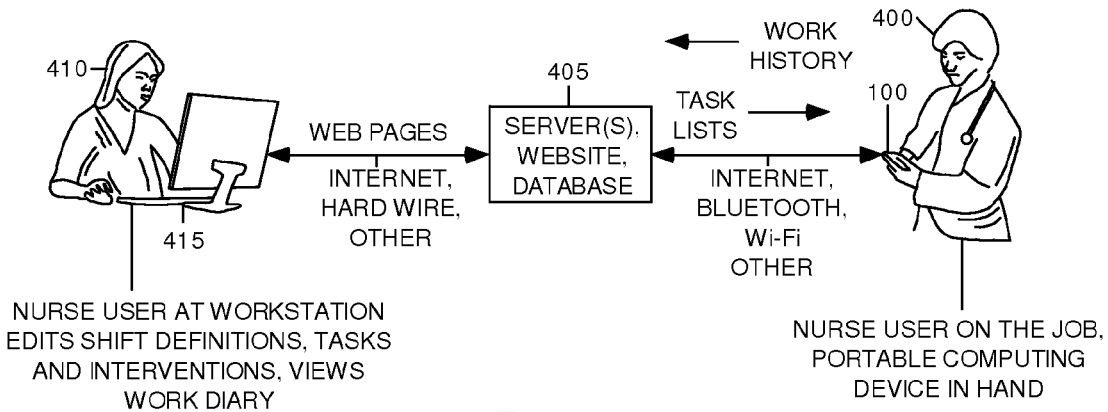
FIGS. 4 and 5 are block diagrams showing hardware that forms an infrastructure for the embodiment in FIGS. 1 through 3.

Infrastructure—FIG. 4

Figure 5:
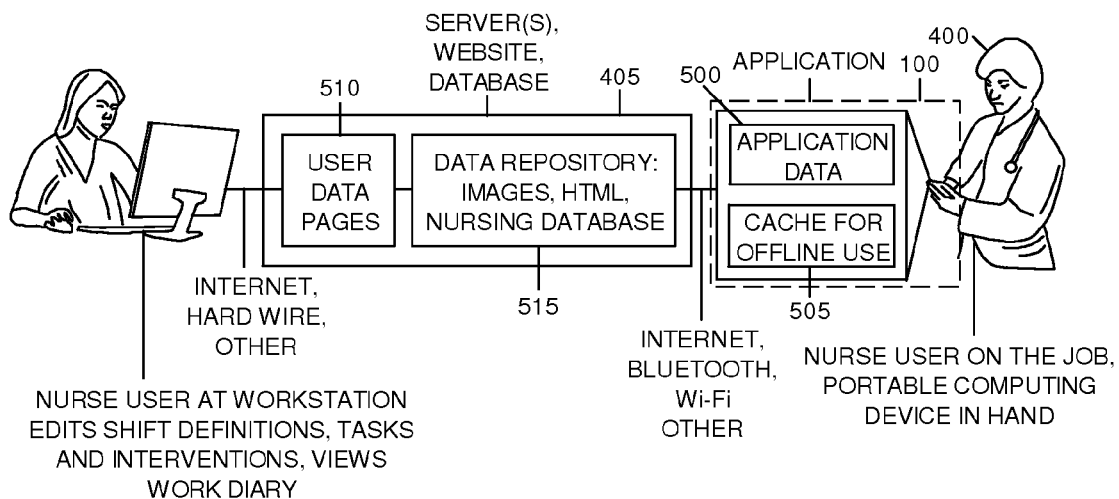

FIGS. 4 and 5 are partial block diagrams showing hardware that forms an infrastructure for operation of the present system. FIG. 4 shows one aspect of the hardware from the perspective of a user. A nurse 400 holds device 100 in one hand while viewing and using the GUI that is part of device 100 (described above). Device 100 communicates wirelessly via the Internet, Wi-Fi, or another means with one or more remote servers 405, i.e., computers arranged to communicate with other computing devices, store data, host websites, etc., that operate an associated website and database. Server 405 is arranged to send task lists to device 100 and to receive work history, i.e., tasks assigned and completed and any other events recorded on device 100. This information is stored in a database associated with server 405. The present system can support the use of more than one device 100 by storing all information associated with each device 100 separately.

Another nurse 410 operates a computer 415 that views the contents of the database associated with server 405. Computer 415 also communicates with server 405 via the Internet or other means. Nurse 410 is able to view and edit the contents of the database and the website associated with server 405, including shift definitions, tasks, and protocols, i.e., information added by nurse 400 while on duty, and view the work diary of nurse 400. The same website also contains the task lists that are sent to device 100 when requested by nurse 400.

Server 405 can be a local server that is shared with others, or the "cloud", i.e. an anonymous remote server with a private account for the present system.

Infrastructure—FIG. 5

FIG. 5 shows one aspect of the hardware comprising the present system from the viewpoint of a system designer, i.e., a person who integrates all the hardware and software that comprise the system associated with device 100. Device 100 is shown as the same handheld device as in FIG. 4, but the description has been expanded to show an application, i.e., the software that runs aspects of the present system that are installed in device 100. This application includes application data 500, i.e., task lists, patient identification, scheduling, etc. as described above and a cache 505 of data and instructions so that device 100 can continue to operate while it is not in communication with server 405. This can happen when device 100 is out of range, i.e., too far from, server 405, when server 405 is not operational, and so forth.

The contents of server 405 are expanded relative to FIG. 4 to show user data pages 510 that hold task lists, work history, and so forth for each device 100. A data repository 515 contains icon images, the ability to communicate with well-known standard Internet protocol HTTP (Hyper-Text Transport Protocol), and the nursing database associated with each of devices 100. Most of the icons represent tasks (e.g. an image of a pill represents medications, the knife/fork represents meals, thermometer represents vital signs, etc.) and others represent patients, badges, and menu items. As the data grows and changes, the collection of icons is frequently updated (e.g., to substitute improved icon images and add new ones), the server dynamically delivers icons to the devices 100. Thus, icons can be added and substituted without having to release new versions of the software that runs on devices 100.

FIRST EMBODIMENT

Operation—FIGS. 1 Through 7

In the example below, the present task scheduling system is used in a hospital setting. The same system or a variation of it is suitable for use in many other scenarios such as manufacturing, delivery, and the like. There may be many instances of device 100 in the same hospital or factory. Each one has its own identification code so that instructions sent to one device 100 will not be duplicated in other devices 100. A separate record and list of tasks is kept for each device.

Entering Patient Data—FIGS. 6 Through 9

Figure 6:
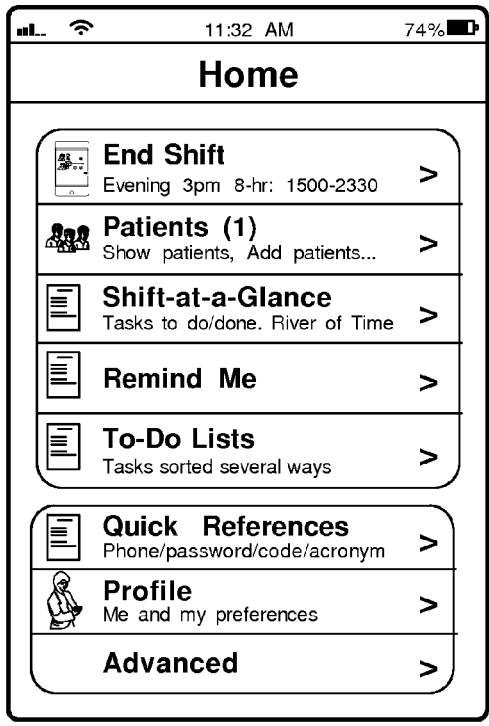
FIGS. 6 through 9 show the appearance of the touch screen of FIGS. 1 through 3 during entry of patient data and tasks to be accomplished during a work shift.

FIG. 6 shows the "Home" screen in display area 102 of device 100. This screen contains various options that are available to the operator of the device. This screen appears when the application is first started and it can always be invoked when desired from any other screen within the GUI.

A patient is assigned to a nurse, either at the beginning of a shift when an incoming nurse "takes report" from an outgoing nurse or during a shift when a new patient is admitted. The nurse invokes the Home screen on device 100 and then selects the "Patients" line as shown in FIG. 6. The arrows at the right of each selection indicate that another screen within the GUI will be activated when the line is selected. In most cases, when device 100 includes a touch screen, the selection is made by simply touching the line.

Figure 7:
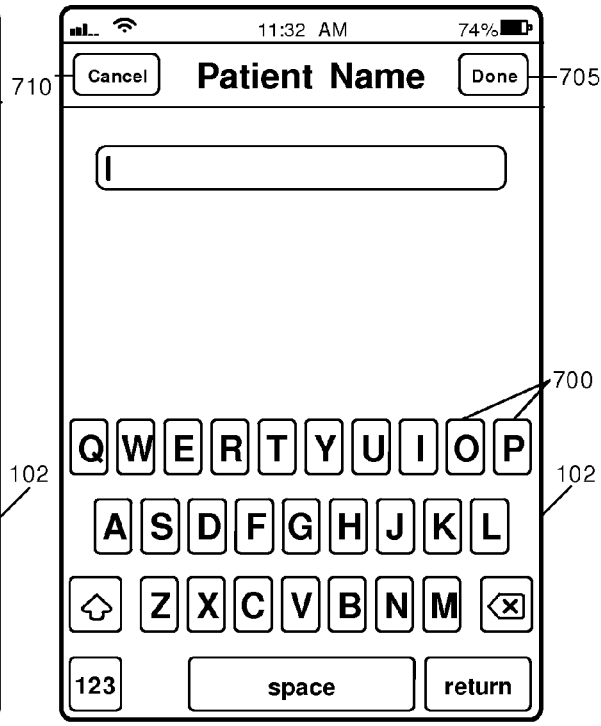

FIG. 7 shows a data entry screen from which data about a patient and their care are entered or updated. When the "Patients" line is selected, a data entry screen (FIG. 8) appears on display 102, replacing the Home screen display (FIG. 6). The nurse now enters the patient's initials or nickname by typing on the various keys 700 (FIG. 7). (The use of the Health Insurance Portability and Accountability Act of 1996—HIPAA-protected patient identifiers is discouraged.) To cancel the name entry process, the nurse selects "Cancel" button 710. To save entered information about the patient and their care, the nurse selects "Done" button 705 to save the patient's name and a new screen appears, as shown in FIG. 8.

Figure 8:
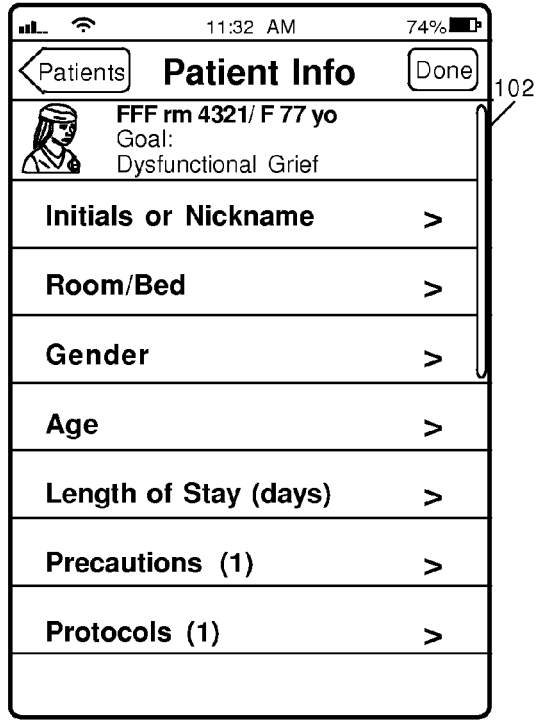
Figure 9:
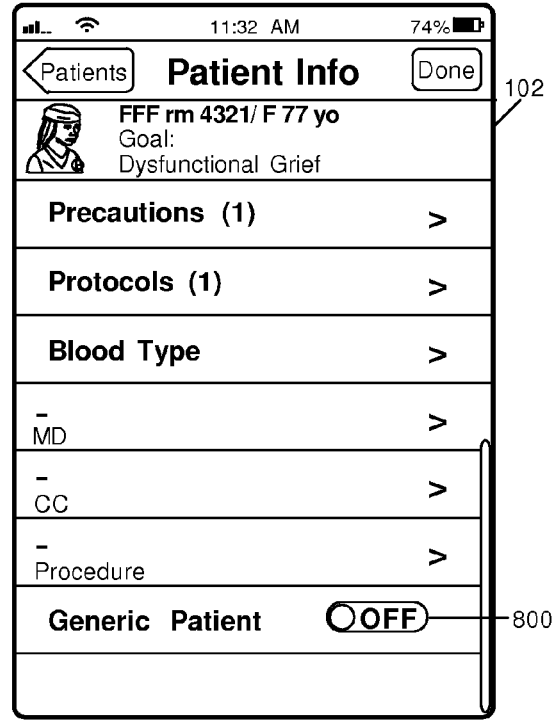

FIGS. 8 and 9 show a new screen that is shown in display area 102 after the nurse selects Done button 705. This is the Patient Information screen. FIG. 9 is the same as FIG. 8 except the screen has been scrolled downward to reveal additional options and information, in well-known fashion. Additional information is entered by selecting among the various offerings shown. In response to selecting some offerings data entry screen the typewriter-like screen of FIG. 7 appears in display 102, as described above. In response to selecting other offerings, a simpler screen can appear, e.g., one in which only M and F are available for entering male or female, respectively, and so forth. An unlimited number of selections can be made available on the Patient Information screen. These include the patient's age, necessary precautions, protocols, blood type, etc. Selection of protocols is particularly important because it causes tasks to be added to the nurse's to-do list. A sliding selector 800 at the bottom of the Patient Information screen can be turned "on" or "off". When selector 800 is "on", the patient being created is designated "generic", meaning that the patient has care requirements that commonly arise (e.g., a patient named "Back Pain") and whose data can thus be repeatedly reused in situations such as Emergency Rooms where there isn't time to enter even small amounts of data afresh each time. In effect, a "generic" patient is a "canned" to-do list that can be reused whenever a patient with that condition is seen. This system is a nursing to-do list, not a medical record, so reusing such data is perfectly acceptable; indeed, it is a time-saver.

Figure 10:
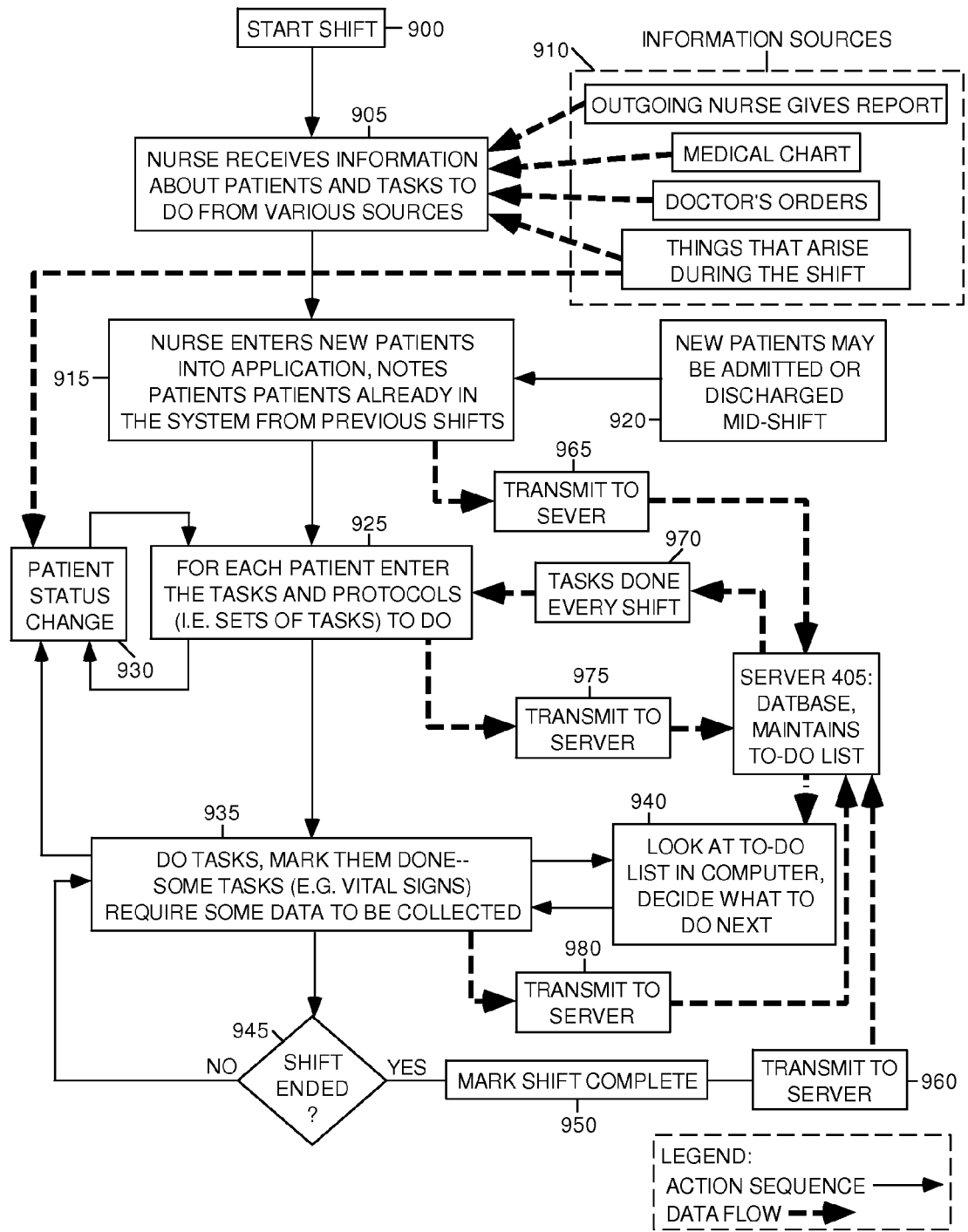
FIG. 10 is a flow chart showing the flow of nurse actions and information according to one aspect of one embodiment.

Action Sequence and Data Flow—FIG. 10

FIG. 10 is a flow chart showing the flow of nurse actions and information according to one aspect of the present embodiment. FIG. 10 shows two processes: the action sequence that the nurse follows and the data flow that occurs as a result of actions taken by the nurse. The action sequence is indicated by lighter, solid lines while the data flow is indicated by heavier, dashed lines. The data and information flows occur between and among nurse 400, device 100, server 405, computer 415, and nurse 410 (FIGS. 5 and 6). The nurse does tasks, marks them done on device 100, and enters data such as those obtained from taking vital signs, etc. (block 935). If the nurse notes a change of status of the patient, the action sequence reverts to block 930, then block 925, and finally back to block 935. The nurse then looks at the To-Do list stored either in device 100 or on server 405 and decides what to do next (block 940). If the shift is not yet over (block 940), the nurse continues doing tasks (block 935). If the shift has ended, the nurse marks the shift "complete" in device 100 (block 945). At this point, the nurse can optionally report any desired information to the next nurse on duty, as in block 905.

The Action Sequence.

At the start of a shift (block 900) the nurse receives information about patients and tasks to do (block 905). The nurse enters new patients into the application and notes patients that were previously entered into device 100 (FIG. 1) or are in the database in server 405 (FIG. 4) (block 915). New patients can be admitted or discharged during a shift (block 920) and this will also be noted as in block 915. The nurse then enters the tasks and protocols for each patient (block 925). If there is a change in the status of a patient (block 930), nurse 400 enters this information (block 925) and then proceeds to do various tasks, mark them done, etc. (block 935). Between tasks, nurse 400 looks at the ROT screen to see what tasks are due soon (or late) (block 940) and selects one or more to do next. If the present shift has not ended, nurse 400 continues doing tasks and looking at the ROT screen (blocks 935 and 940). If the shift has ended, nurse 400 marks the present shift complete in device 100 (block 950). Each action by the nurse causes device 100 to relay an "event" (e.g. a task being marked "completed") to server 405 (block 960). Similarly, when the nurse marks the shift complete, this "event", too, is reported to the server and the application 500 in device 100 (FIG. 5) closes, i.e. terminates.

In addition to the ROT screen which, as described above, serves as a to-do list, this application also offers a more traditional, linear to-do list display (not shown here) that shows the same information. The yet-to-be-done tasks are shown in deadline order at the top of the list, and the done tasks are shown at the bottom. Checking off a task (marking it done) has the same effect as in the ROT: it turns it green. Also, completed tasks are moved to the bottom of the list.

The Data Flow.

At the start of a shift, nurse 400 receives information about patients and tasks to do (block 905). This information is derived from a variety of sources (block 910) including a report from an outgoing nurse, the patient's medical chart, doctor's orders, and things that arise during the shift. Things that arise during the shift, e.g., the patient's condition changes, are also communicated to block 930 so that nurse 400 can enter this information into device 100 (block 925). When nurse 400 enters any new patient information into device 100 (block 915), this information is transmitted to server 405. When nurse 400 enters tasks and protocols into device 100 (block 925), server 405 supplies a list of tasks that are done on every shift (block 970), such as ordering meals, taking vital signs, etc. When any additions or changes occur at block 925, this information is transmitted to server 405 (block 975). As nurse 400 collects data and marks tasks done (block 935) this information is transmitted to server 405 (block 980) by device 100.

There is a constant flow of information between device 100 and server 405 as nurse 400 enters tasks into device 100, performs the tasks, enters information such as vital signs, and marks tasks complete. If for any reason device 100 is lost or not functional, a substitute device 100 can communicate with server 405 and retrieve all information that was present on the original device 100.

Figure 11:
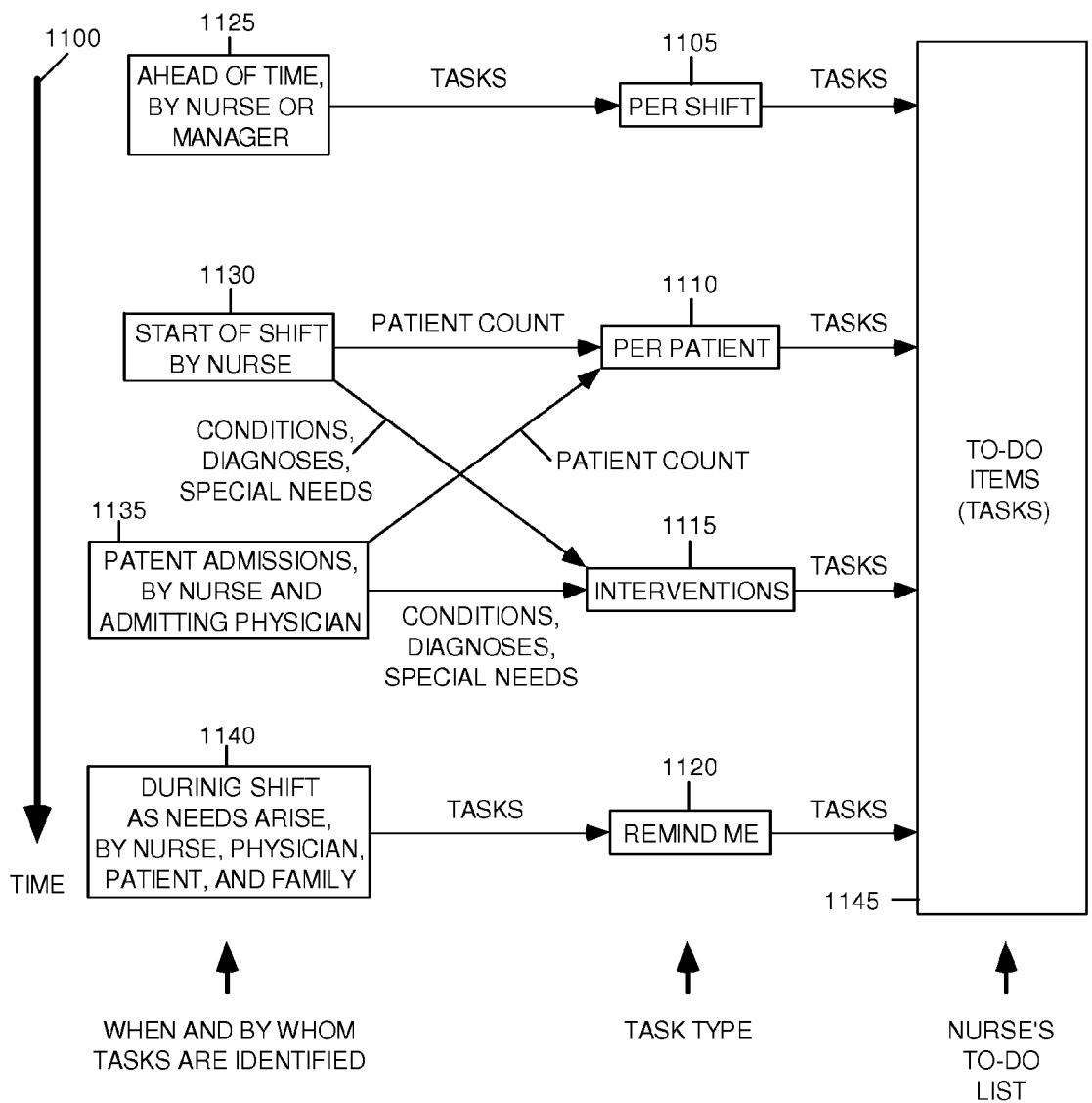
FIG. 11 is a flow chart showing a method for constructing a to-do list according to one aspect of one embodiment.

The to-do List—FIGS. 6, 10, and 11

FIG. 11 is a block diagram showing how various tasks are identified and categorized for addition to a nurse's to-do list for each shift. In one aspect, these tasks are determined in the order indicated by an arrow 1100 at the left of FIG. 11.

A work shift is an 8-, 10- or 12-hour period of time during which the nurse is on the job. The nursing unit can be part of a hospital, long-term care institution, or other inpatient or outpatient medical care facility. Many aspects of this job are routine; much of what the nurse does is the same for every patient on every shift. The challenges are that the list of tasks is long and imposes both substantial memory burdens (remembering everything) and time constraints (getting everything done on time), and that it changes as the shift proceeds. A complete to-do list can be of great value in reducing the nurse's psychological stress and in increasing the completeness with which the required work gets done. Above all, the goal is safe nursing practice, which is enhanced by helping the nurse to remember everything that his or her patients need, and by helping to optimize the use of her limited time on the job. The optimization occurs when the nurse can peruse a complete list of what remains to be done, and prioritize, track, and combine tasks. Without such a list, the nurse must carry all this information in her or his head, which is far more difficult and error prone. The four types of tasks that comprise a complete to-do list are:

1. "Per-shift" tasks (block 1105)—These are the tasks that every nurse does on every shift in a hospital's nursing unit that are not for a specific patient, e.g., restocking a supply cart, taking mandatory breaks, etc. For a given nursing unit, these are known ahead of time (block 1125) and vary little from one shift to another. These tasks, represented by icon 145, are determined prior to the nurse's shift, as indicated by timeline arrow 1100.

2. "Per-patient" tasks (block 1110)—These are tasks that must be done for each patient for which the nurse is responsible on the shift, e.g. setting up a meal tray, administering medications, etc. They are determined at the start of a shift by the nurse (block 1130) and are scheduled next in order on timeline 1100. The total number of tasks is determined by the patient count and the number of patients with special conditions, diagnoses, and needs. For example, if the nurse has five patients, then the "administering medications" task appears five times in the shift definition. These, too, vary little, and in constructing the nurse's to-do list depend only on the number of patients. The number of patients grows when new ones are admitted to the nursing unit; with each, the task list has another set of per-patient tasks added to it. The number is decreased when patients are discharged or transferred from the nursing unit; tasks for those patients that have not yet been marked "completed" (done) are deleted from the list.

3. "Interventions" (also called "protocols") (block 1115)—These are additional sets of tasks that the nurse must do for a particular patient due to a particular need, disease, or condition that the patient has. The need for interventions is determined by the nurse and admitting physician when the patient is admitted (block 1135). For example, if a patient has diabetes, the nurse must perform regular blood glucose tests and administer insulin. Interventions vary according to the needs of the individual patients. They become known when the nurse starting a shift "takes report" from the outgoing nurse (the nurse whose shift is ending and whom the incoming nurse is replacing) and thus learns what diseases, conditions, and special needs her patients have. Interventions are also identified and cause tasks to be added to the to-do list when the nurse examines the medical record, when physicians order them, and/or when new patients are admitted to the nursing unit. When a patient is discharged, any undone tasks belonging to interventions for that patient are deleted from the list.

4. "Remind-me" tasks (1120)—These are tasks whose need arises during the course of the shift, as determined by the nurse, physician, patient, and family (block 1140). For example, if a blood test is required in order to determine a medication dosage, the nurse must remember to retrieve and act upon the test results when they come back from the clinical laboratory. Another example is when a patient's family requests a service such as a phone call to apprise them of the patient's status. Again, this is a task that the nurse must mentally "schedule" for a later time and remember to do it. The "remind-me" task mechanism adds it to the nurse's shift's to-do list. The nurse's complete to-do list (and hence the definition of her shift) consists of the union of these four sets of tasks. These are where the items in the to-do list come from.

The tasks associated with each of these categories are entered into the to-do list (block 1145), as shown above in connection with FIGS. 6 and 10.

Thus, in one aspect this model forms the data structure foundation for software for the nurse to use in keeping track of their work both proactively (as a to-do list, to make sure everything gets done) and retrospectively (as a work history, to record and summarize how she spent her time and what she's accomplished).

CONCLUSIONS, RAMIFICATIONS, AND SCOPE

I have provided an improved task scheduling system and method. A hand-held, portable computing device has an updatable display that shows work to be done and work that is completed during a work day or shift. At the start of a shift, a user of the device enters a plurality of tasks to be completed during the shift. A deadline for the completion of each task is also entered. Near the middle of the display a vertical "bridge" line across the river indicates the present time of day. Using a River of Time metaphor, a series of task icons flow from right to left across the display. The deadline for completion of a particular task is reached when the task icon reaches the bridge line. My system is superior to the previous method of a paper or wall chart for reasons including the following. It is dynamic, updating itself independently, minute-by-minute, to let the worker know how they are doing—keeping up? Falling behind? It is carried by the user in a pocket and can be referred to at any time. It implements some of the best practices in graphical user interface design, such as the fact that recognition is easier than recall. An example of this is how this invention shows overdue tasks flagged with red icons, supporting the cognitive burden of highly technical work and making them visible at a glance. The content of the work (nursing, in this embodiment) is captured in a deep way. Its data structures—shifts, protocols, precautions, tasks, etc.—describe the content of the work to a new level of detail. Thus, it tracks and displays work activities to support on-the-job time management decision-making in a way that no comparable tool can do.

While the above description contains many specificities, these should not be construed as limitations on the scope, but as exemplifications of some present embodiments. Many other ramifications and variations are possible using the system and methods described. For example, the screen's time span—by default, an hour in this embodiment—can instead be a day or a week for an activity wherein the units of work are on a larger scale.

The examples discussed above are drawn from the nursing profession. However the principles shown are applicable to any profession in which the work consists of commonly-repeated sequences of time-sensitive tasks. E.g., in place of the nursing protocols the scheduler can be used for a manufacturing application where "recipes" for assembling various products comprising elementary "to-do lists" can be combined to create the work timeline. Other examples include technical maintenance, construction, bespoke assembly, and numerous roles within healthcare (surgeons, therapists, orderlies, etc.) Any job that can be described as consisting of sequences of discrete, time-sensitive tasks can benefit.

Thus the scope should be determined by the appended claims and their legal equivalents, rather than the examples and particulars given.

The invention claimed is:

1. A system for scheduling tasks to be done during a work period, comprising:
    a. a hand-held portable computing device with a timer and a display screen visible to an operator,
    b. software being executed in said computing device to receive instructions from said operator relating to one or more tasks to be done, one or more times of completion for said respective tasks, and one or more durations of said respective tasks,
    c. said software being executed to display icons or symbols on said display screen representing a patient for whom said tasks are to be done, said tasks, said times of completion of said respective tasks, and said durations of said tasks,
    d. a bridge indicator arranged to indicate the status of said tasks by its position in relation to said icons or symbols on said display screen,
    e. said software also being executed to display one of said icons or symbols that identifies said patient in a fixed position, and continuously move said icons or symbols representative of said tasks in a predetermined direction on said display beneath said one of said icons or symbols that identifies said patient as time of day proceeds a rate determined by said timer,
    f. said software also being executed to cause each of said icons or symbols representing tasks to assume a predetermined color according to the status of its respective task, and
    g. said software further being executed to cause said bridge indicator and said one of said icons or symbols to assume a predetermined condition on said display when a time of completion for each of said tasks is reached,
    h. whereby when said icons or symbols approach said bridge indicator and said operator performs said task represented by said icon or symbol before said icon or symbol reaches said bridge indicator, said task will be performed within said time of completion of said task.

2. The system of claim 1 wherein said software is executed to cause each of said icons that are representative of said tasks to be done to change its appearance when any of said respective tasks to be done is completed.

3. The system of claim 1, further including a server for entering, storing, and exchanging data with said computing device using wireless communication.

4. The system of claim 3 wherein said server is arranged to receive and store information received from said computing device via wireless communication.

5. The system of claim 3 wherein said server is arranged to send instructions to said computing device.

6. The system of claim 3 wherein said software is executed to compile a work history including tasks which are done, remain to be done, are done on time, or are done late, to communicate said work history to said server and to display said work history on said display screen.

7. The system of claim 1, further including a time scale on said display screen, said software being executed to adjust said time scale by means selected from the group consisting of pinching and spreading.

8. The system of claim 1 wherein said software is executed to enable said operator to adjust the position of said bridge indicator.

9. The system of claim 1 wherein said software is executed to add additional tasks, including reminding tasks, to said tasks to be done.

10. The system of claim 1 wherein said software is executed to define a group of said tasks to be done as an intervention or protocol.

11. The system of claim 1 further including identifying said tasks to be done as tasks to be done per shift or tasks to be done per patient.

12. The system of claim 1 wherein said tasks to be done are adjustable by said operator.

13. The system of claim 1 wherein said tasks to be done include mandatory tasks selected from the group consisting of taking breaks, giving reports, receiving reports, providing hygiene and toileting care, ambulation, education, and any other task of nursing work.

14. The system of claim 1 wherein the complete set of said tasks to be done during a shift is created by combining tasks selected from the group consisting of routine, additional, intervention or protocol, per-shift, per-patient, breaks, giving reports, and receiving reports.

15. The system of claim 1 wherein said software in said hand-held portable computing device further includes data entry capability.

16. A method for scheduling at least one task by an operator who has a plurality of tasks to perform, comprising:
    a. providing a timer for supplying the time of day,
    b. providing a hand-held, portable computing device having a touch-sensitive display screen that is visible to said operator, said computing device being responsive to said timer,
    c. providing software executed in said computing device to receive instructions from said operator via touch on said display screen and issue an alarm under a predetermined condition,
    d. providing a stationary icon visible on said display screen and representative of a patient for whom said at least one task is to be performed,
    e. providing a moving icon visible on said display screen and representative of said at least one task, said moving icon being arranged to move across said display screen and beneath said stationary icon representative of said patient in response to said timer supplying said time of day,
    f. providing a bridge indicator displayed on said display screen, said bridge indicator arranged to indicate the status of said at least one task by its position in relation to said moving icon on said display screen, and
    g. instructing said software to place said moving icon on said display screen and to move said moving icon across said display screen at a series of positions representative of said time of day,
    h. said software also being executed to cause said moving icon representing at least one task to assume a predetermined color according to the status of its respective task, and
    i. said software being executed, so that if said operator performs said at least one task before said moving icon reaches said bridge indicator and has provided an instruction to said software indicating that said at least one task has been completed, no alarm will be issued, and when said moving icon coincides with said bridge indicator on said display screen and said operator has not provided said instruction to said software indicating that said at least one task has been completed, said predetermined condition will be satisfied and said alarm will be issued.

17. The method of claim 16 wherein said computing device includes wireless communication ability and said method further includes providing a server computer capable of wireless communication with said computing device.

18. The method of claim 17 wherein said server is arranged to send instructions to said computing device using said wireless communication.

19. The method of claim 17 wherein said computing device is arranged to send data representative of said at least one task and completion of said at least one task to said server.

20. The method of claim 16 wherein said display screen includes a time scale which is adjustable by means selected from the group of touches consisting of pinching and spreading touches.

21. The method of claim 16 wherein said display screen is touch activated.

22. The method of claim 21 wherein said display screen is responsive to two simultaneous touch operations selected from the group of touchings consisting of pinching and spreading touchings.

23. The method of claim 21 wherein said display screen is responsive to a single finger touch operation for sliding the contents of said display screen to a new position within said display screen.

24. The method of claim 21 wherein said operator is a nurse and said tasks are tasks for a patient.

25. The method of claim 16, further including a status display wherein said status display is rendered in a first color and showing items selected from the group consisting of both the minutes of work remaining to be done and the number of minutes remaining in a shift.

26. The method of claim 25, further including rendering said status display in a second color when said number of minutes of work remaining to be done exceeds said number of minutes remaining in a shift.

27. A method for scheduling nursing tasks during a nursing shift, comprising:

a. providing a server containing at least a plurality of nursing task descriptions and patient information,
b. providing a hand-held computing touch-responsive display in periodic communication with said server, said hand-held display being arranged to (a) receive at least said nursing task descriptions and said patient information from said server, and (b) send the status of said nursing tasks to said server,
c. updating said status of said nursing tasks in said hand-held display,
d. providing a fixed icon on said hand-held display indicating said patient information,
e. providing a moving icon on said hand-held display indicating one of said nursing tasks, said moving icon being associated with said fixed icon indicating said patient information, said moving icon arranged to move across said display at a rate equal to the passing of the time of day during said nursing shift, said moving icon further arranged to indicate changes in status of said nursing task by changes of its color,
f. providing a bridge on said hand-held display that indicates the present time of day in a nursing shift, said bridge arranged to indicate the status of said nursing task by its position in relation to said moving icon,
g. providing software executed in said hand-held display so that when said server communicates said descriptions of nursing tasks and said patient information to said hand-held computing display, said hand-held display will display said fixed icon and said moving icon, and said bridge indicator will show the status of said nursing task associated with said patient information as said nursing task is updated.

28. The method of claim 27 wherein said updating is done by touching said touch-responsive display.

29. The method of claim 27 wherein said hand-held computing touch-responsive display is responsive to a reset command that removes all of said task descriptions and patient information from said hand-held computing touch-responsive display.

30. The method of claim 29 wherein said reset command is issued by said server or said updating means in said display.

31. The method of claim 27 wherein said updating means in said hand-held display is responsive to a wi-fi, cellular, or other wireless connection.

* * * * *